(12) United States Patent
Zaveri et al.

(10) Patent No.: US 11,793,746 B2
(45) Date of Patent: Oct. 24, 2023

(54) INTENSE SKIN HYDRATION SYSTEMS AND METHODS

(71) Applicants: Chanda Zaveri, Rancho Palos Verdes, CA (US); Meng Teng Lim, Island East (HK)

(72) Inventors: Chanda Zaveri, Rancho Palos Verdes, CA (US); Meng Teng Lim, Island East (HK)

(*) Notice: Subject to any disclaimer, the term of this patent is extended or adjusted under 35 U.S.C. 154(b) by 0 days.

(21) Appl. No.: 17/060,594

(22) Filed: Oct. 1, 2020

(65) Prior Publication Data
US 2022/0105024 A1 Apr. 7, 2022

(51) Int. Cl.
A61K 8/9783 (2017.01)
A61K 8/64 (2006.01)
A61Q 19/00 (2006.01)

(52) U.S. Cl.
CPC ............. A61K 8/9783 (2017.08); A61K 8/64 (2013.01); A61Q 19/00 (2013.01)

(58) Field of Classification Search
CPC ......... A61K 8/9783; A61K 8/64; A61Q 19/00
See application file for complete search history.

(56) References Cited

U.S. PATENT DOCUMENTS

2008/0213198 A1* 9/2008 Lintner ................... A61K 8/64
514/2.3

OTHER PUBLICATIONS

Jourdan-Salloum (WO 2014128372, using Eng. Trans PE2E). (Year: 2014).*

* cited by examiner

Primary Examiner — Blessing M Fubara
(74) Attorney, Agent, or Firm — Elevated IP, LLC

(57) ABSTRACT

Topical formulations comprising a dipeptide having a sequence of Lys-Pro, optionally complexed with an amino add, and at least one bioflavonoid or bioflavonoid extract in a cosmetically or pharmaceutically acceptable carrier provide intense skin hydration and improve skin texture and appearance.

19 Claims, 6 Drawing Sheets
Specification includes a Sequence Listing.

INTENSE SKIN HYDRATION SYSTEMS AND METHODS

CROSS-REFERENCE TO RELATED APPLICATIONS

None.

INCORPORATION OF SEQUENCE LISTING

This document incorporates by reference herein an electronic sequence listing text file, which was filed in electronic format via EFS-Web on Nov. 4, 2022. The text file is named "25-19_US_Seq_Listing_ST25.txt," is 476 bytes, and was created on Nov. 4, 2022.

BACKGROUND

The dermis is the largest constituent of the skin, occupying nearly 90% of the skin's total volume. Its composition imparts to the skin the favorable mechanical properties of firmness, elasticity and tone. Casual observation exemplifies the loss of these properties over time. As the major water reservoir for the skin, the dermis expends, during the lifetime of an organism, nearly 60% of the skin's water content to the processes of intrinsic (genetic) and extrinsic (environmental) aging. Taken collectively, the degenerative processes that originate in the dermis correspond to a decrease in the ability of the cell, particularly the fibroblast, to regenerate and synthesize the macromolecules that constitute the extracellular matrix.

The primary macromolecules of the dermis, namely collagen and elastin, establish a three-dimensional connective tissue network that is bathed in ground substance and cellular matter. In particular, fibrillar collagen assumes the dominant role as the most abundant macromolecule, ensuring the mechanical properties and structural integrity of all its constituent tissues. Within the skin, fibrillar collagen is uniquely vulnerable to environmental trauma and degradation, which leads, in part, to aging.

Peptide signal sequences are powerful messengers that may affect cellular metabolism, the cell cycle, and the cellular response to stress. Signal sequences are generated during the translation of genetic information into protein structures and are commonly found at the terminal ends of the protein strand. During the post-translational modification of a protein, the signal sequence is cleaved, which enables it to exert one or more biological activities. The traditionally recognized role of signal sequences has been to exert negative or positive feedback controls on the synthesis of their precursor molecules.

SUMMARY

The present invention relates to a novel peptide signal sequence that has been shown in early testing to significantly reverse some of the in vitro endpoints of cutaneous aging with positive clinical correlation. The signal sequence described has several independent mechanisms of action that include selective, dose-dependent fibroblast proliferation, an increase in the metabolic activity of the skin, an increase in collagen I and III synthesis as measured by a proline incorporation assay (with more than twice the end result when compared to retinoic acid 0.025%), depression of tyrosinase activity, and a down-regulatory effect on proinflammatory prostaglandins in in vitro three-dimensional skin models. In vivo test results have demonstrated a significant acceleration of the wound healing response with associated anti-erythema properties. Pilot clinical studies have revealed an average 8% increase in epidermal thickness six weeks after application and a high level of patient satisfaction ($p=0.0225$) regarding qualitative cosmetic changes in a population previously treated with retinoic acid or chemical peels.

Recent discoveries have shown that a hydrolytic fraction of native collagen is able to stimulate the growth of fibroblast-like cells and induce novel collagen synthesis and excretion. Subsequent in vitro experiments have shown that very low concentrations of this signal sequence are able to induce extracellular collagen synthesis by dermal fibroblasts without inducing malignant transformation.

Modification of this peptide generated a novel peptide signal sequence with no known natural biological correlate. Fibroblast proliferation demonstrated a dose-dependent response, with the deposition of collagen I and III at a ratio of 1:3 in the dermal matrix. Proline incorporation was followed as a precursor to collagen deposition, and was found to be more than twice that of Retin-Am™ 0.025%. Competitive inhibition of tyrosinase activity led to depressed melanin synthesis, and an anti-inflammatory effect was demonstrated in parallel studies against indomethacin and actual examinations of inflammatory cytokine and prostaglandin production. In vivo testing revealed significant trophic effects in laboratory and clinical settings, both cosmetic and reconstructive.

In an aspect, a topical formulation comprises a dipeptide having a sequence of Lys-Pro and at least one bioflavonoid in a cosmetically or pharmaceutically acceptable carrier. In an embodiment, the bioflavonoid is a bioflavonoid extract.

In an embodiment, the at least one bioflavonoid is selected from the group consisting of flavones, flavonols, flavanones, flavanols, anthocyanins and isoflavones.

In an embodiment, the at least one bioflavonoid is derived from a source selected from the group consisting of yam, ruscus, ivy, Indies chestnut, focus vesiculosus, broccoli, parsley, thyme, legumes, buckwheat, berries, bananas, citrus fruits, onion, red wine, dark chocolate, tea, or Ginko *biloba*.

In an embodiment, the at least one bioflavonoid is a yam extract, such as but not limited to Wild Mexican yam (e.g., *Dioscorea mexicana* or *Dioscorea* composite) extract.

In an embodiment, the at least one bioflavonoid is present in a concentration between 2 wt % and 30 wt %, or between 5 wt % and 25 wt %, or between 9 wt % and 20 wt %, or between 12 wt % and 18 wt %.

In an embodiment, the dipeptide and the at least one bioflavonoid are present in a weight ratio between 0.25:15 and 1:3, or between 0.3:15 and 1:5, or between 0.5:15 and 1:6, or between 1:15 and 1:7. In an embodiment, the dipeptide and the at least one bioflavonoid are present in a weight ratio of 1:30, or 1:15, or 1:9.

In an embodiment, the dipeptide and the at least one bioflavonoid are present in the topical formulation at a concentration of at least 10% by weight, or at least 12% by weight, or at least 15% by weight. In an embodiment, the dipeptide and the at least one bioflavonoid are present in the topical formulation at a concentration between 10% by weight and 25% by weight, or between 12% by weight and 20% by weight.

In an embodiment, the topical formulation further comprises a polypeptide having a sequence of Asp-His-D-Phe-Arg-Trp (SEQ ID NO: 1).

In an embodiment, the topical formulation further comprises one or more of ruscus extract, ivy extract, Indies chestnut extract, gingko extract, and fucus vesiculosus extract.

In an embodiment, the topical formulation further comprises at least two bioflavonoids.

In an embodiment, the topical formulation further comprises an amino acid selected from the group consisting of glycine, alanine, proline and combinations thereof. In an embodiment, the amino acid is complexed with the dipeptide. For example, the amino acid and the dipeptide may be covalently bound to one another, or the amino acid and the dipeptide may be ionically bound to one another, or the amino acid and the dipeptide may be electrostatically attracted to one another.

In an embodiment, the cosmetically or pharmaceutically acceptable carrier is selected from the group consisting of water, an organosilicone compound, a silicone elastomer, a $C_6$-$C_{28}$ linear hydrocarbon and combinations thereof.

In an aspect, a method of hydrating skin in a subject in need thereof comprises administering to the subject a therapeutically effective amount of a topical formulation disclosed herein. In an embodiment, the therapeutically effective amount is administered in portions once daily, twice daily or three times daily. In an embodiment, the topical formulation is administered topically or transdermally. In an embodiment, the topical formulation is administered as a lotion, an oil, a cream, a butter, or a serum.

DETAILED DESCRIPTION

Figure 1:
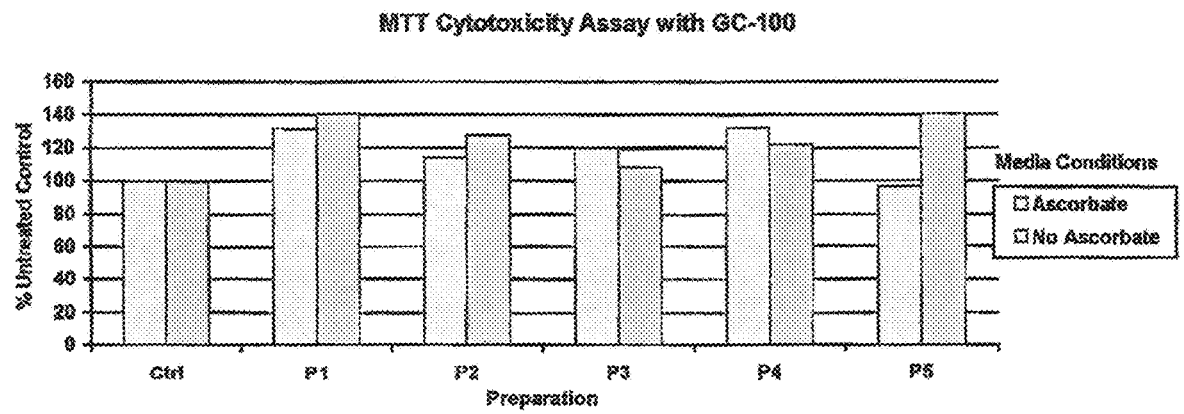
FIG. 1 is a graph showing MTT cytotoxicity assay results, according to an embodiment.

In general, the terms and phrases used herein have their art-recognized meaning, which can be found by reference to standard texts, journal references and contexts known to those skilled in the art. The following definitions are provided to clarify their specific use in the context of this description.

An "amino acid" is a molecular building block of protein.

An "amino acid residue" is the simplest discreet unit or monomer of a protein chain.

A "complex" is a chemical entity formed by coupling (e.g., electrostatically) or bonding (e.g., covalently or ionically) two molecules.

A "conjugate" is a chemical entity formed by coupling or bonding two chemical moieties. In an embodiment, a conjugate is a chemical molecule formed by covalently or ionically bonding two chemical moieties.

A "bioflavonoid" or "flavonoid" is a chemical having a 15-carbon (C6-C3-C6) skeleton comprising two phenyl rings and a fused heterocyclic ring. Bioflavonoids are derived from plants or fungus.

In an embodiment, a "serum" is a product with a high concentration of active substances that are rapidly absorbed. Skincare serums are typically applied topically after cleansing and before moisturizing.

"Optical isomers", "diastereomers", and "geometric isomers" of some of the compounds represented by the formulae described herein are comprehended to be within the scope of the instant invention, as well as racemic and resolved enantiomerically pure forms and pharmaceutically acceptable salts thereof.

"Optical purity" is a comparison of the optical rotation of a pure sample of unknown stereochemistry versus the optical rotation of a sample of pure enantiomer. It is expressed as a percentage, where 0% indicates a 50/50 racemic mixture and 100% indicates an enantiomerically pure sample.

New Signal Sequence

A new signal sequence, particularly, a dipeptide that improves transdermal delivery and/or absorption of bioflavonoids is disclosed herein. The new signal sequence has the amino acid sequence:

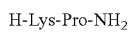

Standard three letter codes are used to designate the amino acids. Accordingly; the dipeptide above contains the amino acids: Lysine-Proline Methods of Dipeptide Synthesis One method of producing a dipeptide involves chemical synthesis. This can be accomplished using solid phase methodologies well known to those skilled in the art. (See, e.g., Stewart; J. M. & Young, J. D. "Solid Phase Peptide Synthesis" Pierce Chemical Co. Rockford, Ill. 1984; Merrifield, J. Am, Chem. Soc., 85:2149 1964; Houghten, Proc. Natl. Acad. Sci. USA 82:5132 1985; and U.S. Pat. Nos. 4,105,603; 3,972,859; 3,842,067; and 3,862,925).

The condensation between two amino acids, or an amino acid and a peptide, or a peptide and a peptide can be carried out according to the usual condensation methods such as the azide method, mixed acid anhydride method, DCC (N,N'-dicyclohexylcarbodiimide) or DIPC (N,N'-diisopropylcarbodiimide) methods, active ester method (ρ-nitrophenyl ester method), BOP benzotriazole-1-yl-oxy-tris (dimethylamino) phosphonium hexafluorophosphate method, N-hydroxysuccinic acid imido ester method, etc., and Woodward reagent K method.

Amino Acid Substitutions

It is a well established principle of protein and peptide chemistry that certain amino acid substitutions, entitled "conservative" amino acid substitutions, can frequently be made in a protein or a peptide without altering either the conformation or the function of the protein or peptide.

Conservative substitutions may be employed in the synthesis of proteins, peptides or analogs disclosed herein. Accordingly, peptides having conservative amino acid substitutions are within the scope of the present invention. Such changes include substituting any of isoleucine (I), valine (V), and leucine (L) for any other of these amino acids; aspartic acid (D) for glutamic acid (E) and vice versa; glutamine (O) for asparagine (N) and vice versa; and serine (S) for threonine (T) and vice versa. The above-mentioned substitutions are not the only amino acid substitutions that can be considered "conservative." Other substitutions can also be considered conservative, depending on the environment of the particular amino acid. For example, glycine (G) and alanine (A) can frequently be interchangeable, as can be alanine and valine. Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Cysteine (C) can frequently be replaced by serine (S) when cysteine's capacity to form disulfide bonds is either undesirable or unneeded. Still other changes can be considered "conservative" in particular environments.

Cosmetic and Pharmaceutical Compositions

In general, a cosmetic or pharmaceutical composition of the present invention comprises a dipeptide and at least one bioflavonoid in a therapeutically effective amount and an acceptable carrier, excipient or diluent.

The therapeutically effective amount can be determined by one of ordinary skill in the art, with reference to the dosages described herein.

Conventional acceptable carriers known in the art can include alcohols, e.g., ethyl alcohol; serum proteins, cholesterol, human serum albumin, liposomes, buffers such as phosphates, water, sterile saline or other salts, electrolytes, glycerol, hydroxymethylcellulose, propylene glycol, polyethylene glycol, polyethylenesorbitan, other surface active agents, vegetable oils, and conventional anti-bacterial or anti-fungal agents, such as parabens, chlorobutanol, phenol, sorbic acid, and the like. A cosmetically acceptable carrier or a pharmaceutically acceptable carrier within the scope of the present invention meets industry standards for sterility, isotonicity, stability, and non-pyrogenicity. In an embodiment, a cosmetically or pharmaceutically acceptable carrier suitable for use in a disclosed composition is selected from the group consisting of water, an organosilicone compound, a silicone elastomer, a $C_6$-$C_{28}$ linear hydrocarbon and combinations thereof.

The active ingredient is often mixed with diluents or excipients that are physiologically tolerable and compatible with the active ingredient(s). Suitable diluents and excipients are, for example, water, saline, dextrose, glycerol, or the like; and combinations thereof. In addition, if desired the compositions may contain minor amounts of auxiliary substances such as wetting or emulsifying agents, stabilizing or pH-buffering agents, and the like. For a more detailed description of the foregoing see a standard pharmaceutical text such as Remington's Pharmaceutical Sciences, Mack Publishing Co. Easton, Pa. (1970).

Methods of Use

The compounds of this invention are shown to hydrate skin and improve skin texture and appearance.

Administration

Compositions according to the present invention can be administered by a number of routes. They are typically administered topically or transdermally.

The dosages to be administered can be determined by one of ordinary skill in the art depending on the clinical severity of the condition, the age, sex and weight of the patient, the exposure of the patient to conditions that may affect the course of treatment, the existence or nonexistence of underlying systemic problems such as diabetes, impaired circulation, and immunocompromised status, and other pharmacokinetic factors generally understood in the art, such as liver and kidney metabolism. The interrelationship of dosages for animals of various sizes and species and humans based on $mg/m^3$ of surface area is described by E. J. Freireich et al., "Quantitative Comparison of Toxicity of Anticancer Agents in Mouse, Rat, Hamster; Dog; Monkey and Man," Cancer Chemother. Rep. 50:219-244 (1966). Adjustments in the dosage regimen can be made to optimize the therapeutic response. Doses can be divided and administered on a daily basis or the dose can be reduced proportionally depending on the therapeutic situation.

Methods according to the present invention can be used to treat humans or socially or economically important animal species such as dogs, cats, horses, sheep, cows, goats, or pigs. Methods according to the present invention are not limited to use in humans.

The invention is illustrated by the following Examples. These Examples are for illustrative purposes only and are not intended to limit the invention.

An artificial, metabolically active three-dimensional skin model was used in this series of experiments to study the response to a novel peptide signal sequence, GC-100, in redefined conditions. The results obtained with the chosen skin analog fully confirm the data obtained from fibroblasts cultured in a monolayer system. Animal and human studies illustrated the biostimulating activity of GC-100 on both epidermal and dermal cell populations. Examined together, it is reasonable to conclude that GC-100 contributes to the synthesis of a substantial extracellular matrix, enhances local dermal and epidermal metabolic activity, and contributes to the regeneration and rejuvenation of the skin.

Example 1: Skin Analog

Preclinical studies used a three-dimensional metabolically and mitotically active in vitro human skin analog, Skin²™. This human skin substrate consists of neonatal foreskin fibroblasts that secrete a functionally active extracellular matrix grown on a medical-grade nylon mesh cocultured with human neonatal foreskin keratinocytes that differentiate into a multilayered epidermis.

The constituents of the dermal compartment, which include collagen types I, III and V; fibronectin; decorin; tenascin; and sulfated and non-sulfated glycosaminoglycans, are generated exclusively by the resident fibrolasts, which demonstrate a density comparable to neonatal and adult dermis at 7-11 nuclei/$6.8 \times 10^{10}$ $\mu m^3$ of dermis. The collagen proportions in this analog are similar to fetal skin. The collagen fibrils demonstrate mature, cross-linked architecture with typical 67-nm periodicity and variable thickness reminiscent of in vivo findings. The dependence of collagen matrix synthesis of the presence of ascorbate was confirmed by analyzing for hydroproline using HPLC.

Keratinocytes of the epidermal compartment differentiate into distinct basal, spinous granular and stratum corneum layers that display the appropriate differentiation markers that enable the correlation of this epidermal analogue with human specimens in viva A well-developed basement membrane consisting of a *Lamina densa, Lamina lucida*, anchoring filaments, hemidesmosomes, tonofilaments, and elastin-associated microfibrils are evident on scanning electron micrographs. Histologic analysis reveals a basal *lamina* containing collagen type IV, laminin, nidogen, and heparin sulfate.

The metabolic activity of this human skin analog, despite the absence of additional cell populations resident in normal skin, is qualitatively and quantitatively comparable to human skin samples in vivo. The release of immunomodulatory and inflammatory mediators, such as IL-1a, t-PA, gelatinase, and other cytokines and prostaglandins, in response to cutaneous irritants or environmental stresses excludes the primary role of Langerhans cells or infiltrating immune cells in inflammatory reactions.

Unique to this human skin analog is its ability to support an increase in collagen synthesis and deposition in the presence of retinoids and corticosteroids. These findings confirm that when dermis is cocultured with differentiating keratinocytes, fibronectin, hyaluronic acid and collagen deposition increase secondary to intracellular communication between epidermis and dermis. This coculture system has also demonstrated that increased fibronectin deposition is a wound model is modulated by keratinocyte elaboration of growth factors such as TGF-β and EGF rather than from local fibroblasts. In summary, fibroblasts play little to no role in fibronectin deposition in the wound model, whereas keratinocytes can exert a minimal effect on dermal activity such as collagen deposition.

Example 2: Pharmacotoxicological Testing

This Example tested cellular viability and measured cell respiration in vitro in response to the application of GC-100 preparations. Topical skin preparations were shown to have an acceptable cytotoxic response of 80% of untreated controls.

The toxicity of a substance can be quantified by sustained metabolic activity of the cell in the presence of test substance. The integrity of cellular metabolism can be evaluated using the MTT Coloration Assay, which relies on the metabolism of 3-[4,5-dimethylthiazol-2-yl]-2,5-diphenyl tetrazolium bromide by succinate dehydrogenase of the citric acid cycle. Since the metabolism of MTT is dependent on mitochondrial activity, the amount of metabolite produced can be correlated with the number of viable cells present per well. The metabolite concentration is measured via spectrophotometry, with the absorption value converted to an absolute number that describes cellular growth. MTT cytotoxicity assay results are shown in FIG. 1.

GC-100 does not elicit a cytotoxic response, which is traditionally indicated by levelse below 80% of untreated control. The observed increase above untreated control may be attributed to a phenomenon called hormesis, which is observed when cellular metabolism is increased in the presence of a test material. This can translate into an increase mitochondrial function and a rise in MTT greater than that of the untreated control.

Figure 2:
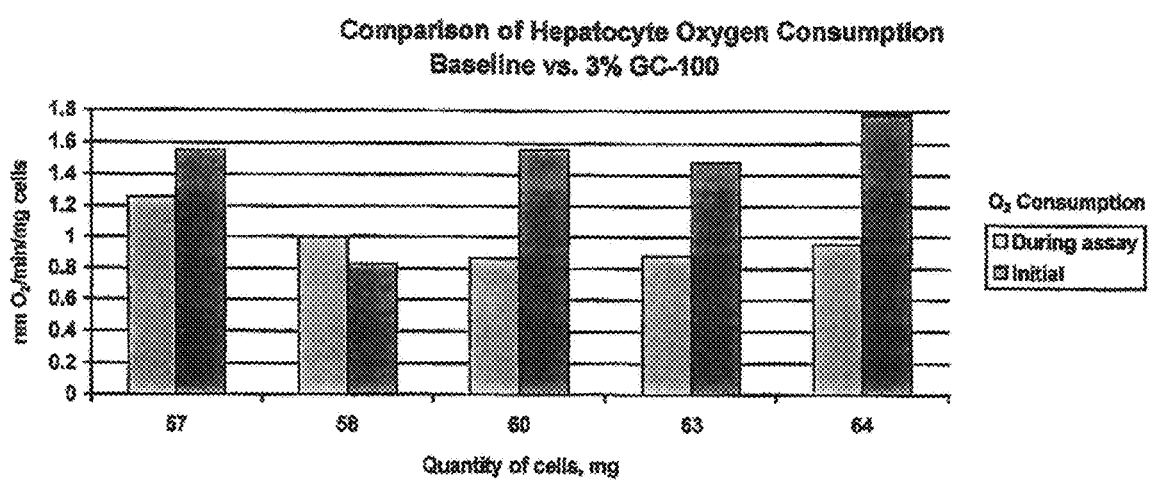
FIG. 2 is a graph showing hepatocyte oxygen consumption at baseline and in the presence of 3% GC-100, according to an embodiment.
Figure 3:
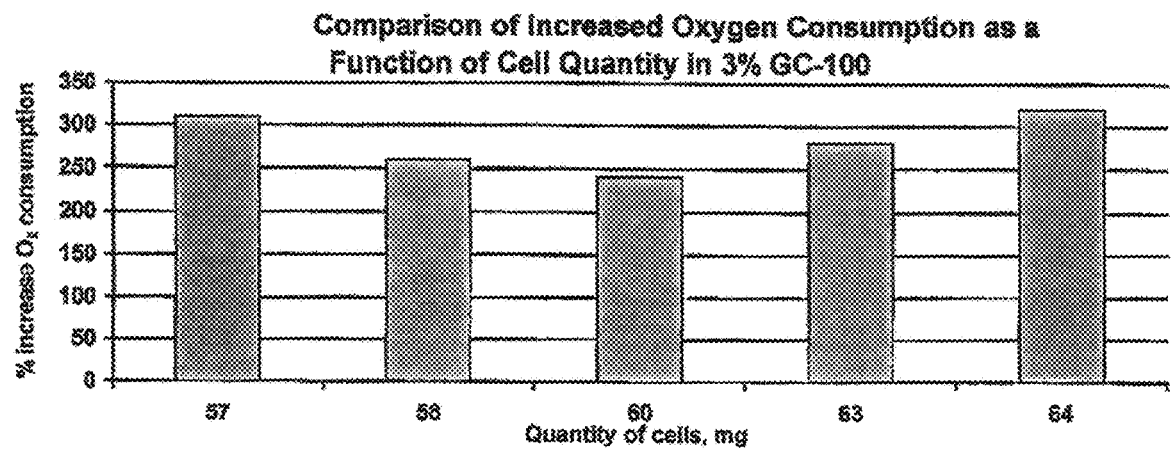
FIG. 3 is a graph showing increased oxygen consumption as a function of cell quantity in the presence of 3% GC-100, according to an embodiment.
Figure 4:
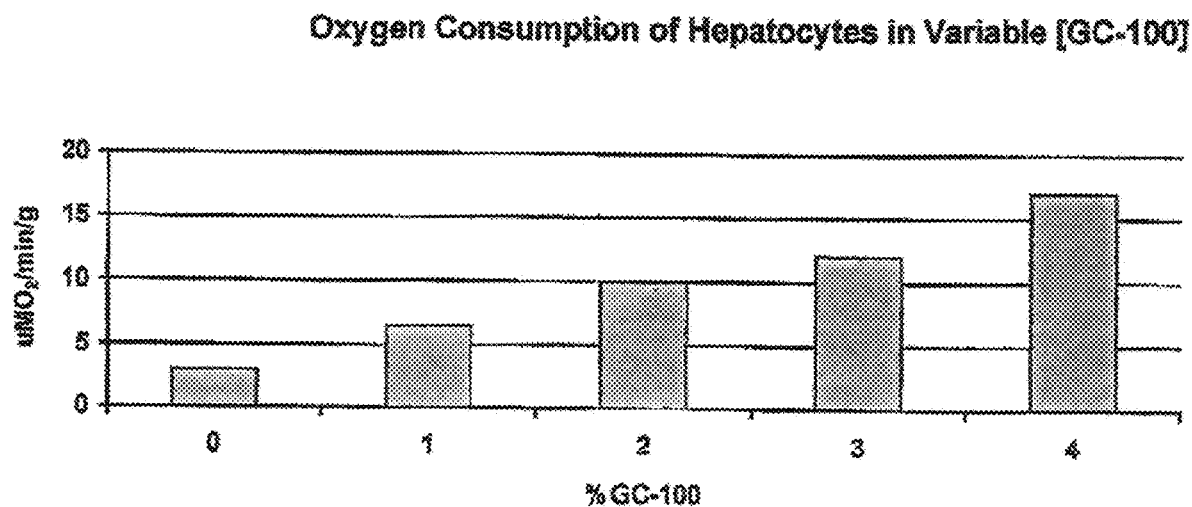
FIG. 4 is a graph showing hepatocyte oxygen consumption in the presence of GC-100 at various concentrations, according to an embodiment.

The measurement of increased intracellular oxygen consumption demonstrates the efficacy of an active substance at the cellular level. Increased cellular respiration may be equated with more efficient use of cellular reserves (e.g., polysaccharides & triglycerides) and improved elimination of metabolic waste. The end result of enhanced cellular respiration is cellular regeneration and restoration of the organ system being evaluated. The activation of cellular respiration can be evaluated using an oxygraph. Since the oxygraph electrode response is directly proportional to the concentration of dissolved $O_2$ in the test media, a measure of cellular $O_2$ consumption can be calculated to yield information on changes in cellular respiration. The results are shown in Table 1 and FIGS. 2-4, where ha is the $O_2$ consumption of fresh cell preparations in the assay phase with 3% GC-100 and he is the $O_2$ consumption of fresh cell preparations in the control phase. FIG. 2 is a graph showing hepatocyte oxygen consumption at baseline and in the presence of 3% GC-100, FIG. 3 is a graph showing increased oxygen consumption as a function of cell quantity in the presence of 3% GC-100. FIG. 4 is a graph showing hepatocyte oxygen consumption in the presence of GC-100 at various concentrations.

TABLE 1

$O_2$ CONSUMPTION PROFILE: 3% GC-100

| Quantity of cells, mg | Initial consumption, hc nm $O_2$/min/mg cells | Final consumption, ha | % increase $O_2$ consumption |
| --- | --- | --- | --- |
| 57 | 1.558 | 1.259 | 310 |
| 58 | 0.828 | 1.003 | 260 |
| 60 | 1.564 | 0.865 | 240 |
| 63 | 1.482 | 0.879 | 280 |
| 64 | 1.785 | 0.954 | 320 |

As shown in FIG. 2, the average increase in $O_2$ consumption in the presence of 3% GC-100 is 282%±30, which is demonstrative of increase cellular respiration and metabolic activity. FIG. 3 shows that oxygen consumption in the presence of a fixed percentage of GC-100 appears to be independent of the concentration of hepatocytes with no clear trend demonstrated for the concentrations tested. In FIG. 4, an increase in the concentration of GC-100 between 0 and 4% results in a similar increase in the oxygen consumption profile of hepatocytes in culture.

Example 3: Dermopharmacological Testing

This Example quantifies the biostimulating activity of GC-100 on human diploid fibroblasts in a suboptimal nutritional environment.

Figure 5:
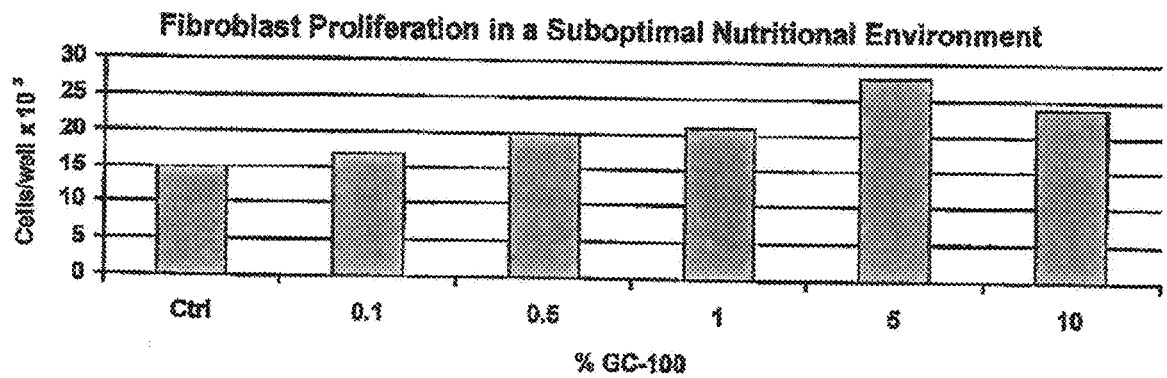
FIG. 5 is a graph showing fibroblast proliferation in a suboptimal nutritional environment, according to an embodiment.

Cellular proliferation, or mitotic activity, will be assessed using an MTT assay. MTT added to the microtiter wells is metabolized by succinate dehydrogenase of the citric acid cycle. Since the metabolism of MTT is dependent on mitochondrial activity, the amount of metabolite produced can be correlated with the number of viable cells present per well. The metabolite concentration is measured via spectrophotometry, with the absorption value converted to an absolute number that describes cellular growth based on standardized curves. The results are shown in Table 2 and FIG. 5, which is a graph showing fibroblast proliferation in a suboptimal nutritional environment.

TABLE 2

FIBROBLAST PROLIFERATION in suboptimal nutritional medium

| [GC-100] | Cells/well ($\times 10^3$) |
| --- | --- |
| CONTROL | 15 |
| 0.1% | 17 |
| 0.5% | 20 |
| 1.0% | 21 |
| 5% | 28 |
| 10% | 24 |

Cumulative fibroblast proliferation (mitosis) in the presence of GC-100 is 83%.

GC-100 appears to provide the nutritional supplementation necessary for fibroblast proliferation in the presence of a suboptimal nutritional environment, with an increasing rate of proliferation as the concentration of GC-100 is increased up to 5%.

The dermotrophic effect of GC-100 was also determined using lysyl oxidase levels as an endpoint to determine whether GC-100 can effect the concentration of lysyl oxidase in wounded tissues and to establish whether GC-100 can accelerate the wound healing process using qualitative measurements.

Materials and Methods

Nude mice were chosen because their skin (and their lack of hair) is more similar to human skin than are other commonly used laboratory test animals. The test population was divided into 4 groups of 10 nude mice for the purpose of examining the best application sequence for GC-100 relative to injury. Group definitions are as follows:

| GROUP | PHASE OF GC-100 APPLICATION RELATIVE TO INJURY |
|---|---|
| Control | None |
| II | Pretreatment |
| III | Post-treatment |
| IV | Pre- & Post-treatment |

A surgical wound measuring 2.54 cm in length and penetrating the dermis was made on the right hind quarter of all test subjects after appropriate anesthesia was administered.

A second index of injury using 1% xylene was used in all test subjects after creation of the surgical wound. Using a sterile tuberculin syringe, 0.1 mL of a 1% xylene solution was injected subcutaneously into the region of the surgical wound. The final size of the injury measured $25 \times 20$ mm$^2$.

The mice in Groups II, III, and IV were divided randomly after physical and chemical injury into 2 subgroups of 5 mice each for application of either GC-100 0.5% or 1%. Pretreatment for Group II and IV mice was conducted one hour prior to any injury, where GC-100 0.5% and 1% was rubbed into the right hind quarter of the designated mice for 50 cycles using a nylon glove. Post-treatment for mice in Group III and IV with GC-100 0.5% and 1% was conducted immediately after injury.

Figure 6:
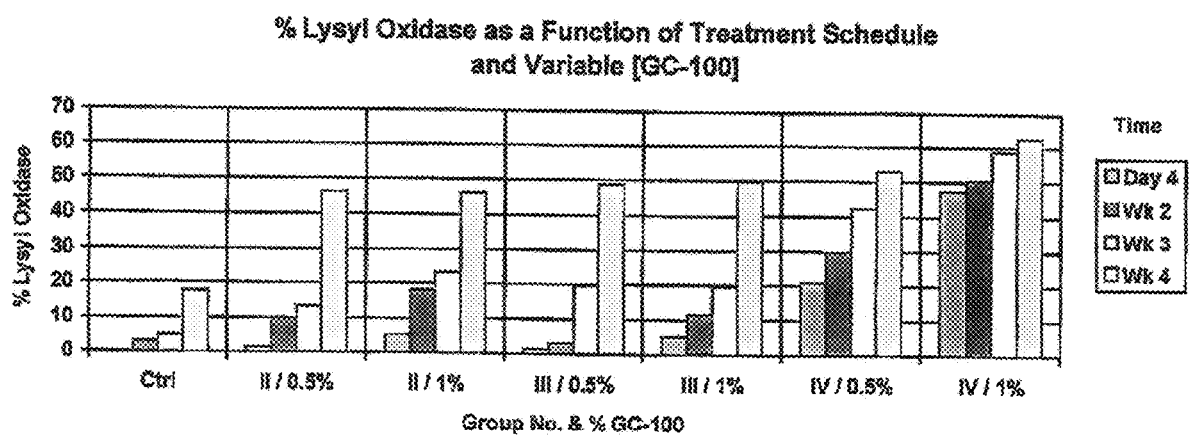
FIG. 6 is a graph showing percent lysyl oxidase as a function of treatment schedule and GC-100 concentration, according to an embodiment.

Wound recovery was determined over 30 days using cutaneous punch biopsies that were taken on post injury day 4, and at the conclusion of weeks 2, 3, and 4 from the wound margins. Biopsy specimens were analyzed for lysyl oxidase activity using a standard assay. Results are shown in Table 3 and FIG. 6, which is a graph showing percent lysyl oxidase as a function of treatment schedule and GC-100 concentration.

TABLE 3

| | | % LYSYL OXIDASE | | | |
|---|---|---|---|---|---|
| GROUP | [GC-100] | Day 4 | Week 2 | Week 3 | Week 4 |
| I | NONE | 0.0 | 3.1 | 4.8 | 17.7 |
| II | 0.5% | 1.4 | 10.2 | 13.4 | 45.9 |
|  | 1% | 5.2 | 18.2 | 23.4 | 45.9 |
| III | 0.5% | 1.2 | 3.2 | 19.8 | 48.7 |
|  | 1% | 5.3 | 11.5 | 19.7 | 49.6 |
| IV | 0.5% | 21 | 30.1 | 42.4 | 52.8 |
|  | 1% | 47.2 | 50.5 | 58.8 | 62.7 |

A radial forearm free-flap was used to demonstrate the trophic effect of GC-100. The superior half of the flap was treated with GC-100 three times over 9 days, beginning on postoperative day 14, Upon physical examination, the treated skin was noticeably thicker, smoother and less erythematous.

GC-100 significantly increases the local concentration of lysyl oxidase in a treated environment after physical and chemical injury. Lysyl oxidase plays a major role in the transitional and remodeling phases of wound repair, where it stabilizes the wound (via collagen cross-linking) prior to and during fibroblast-mediated wound contraction.

GC-100 demonstrates a significant regenerative capability in the free flap full-thickness skin graft model. Generalized healing is accelerated by 50% on skin overlying a muscle belly, with accelerated normalization of the grafter skin to resemble native skin.

Example 4: Efficacy Testing

This Example evaluates [$^3$H]-Proline incorporation as a measure of potential collagen deposition in the presence of GC-100 to determine the ability of GC-100 to stimulate proline incorporation, to determine the influence of local ascorbic acid concentration on proline incorporation, to compare proline incorporation stimulated by GC-100 with that stimulated by Retin-A 0.025%, and to illustrate histologically the effect of GC-100 on collagen deposition.

Quantifying proline incorporation can be used to measure potential collagen deposition stimulated by a test substance. This concept is the foundation for the following experiments.

Figure 7:
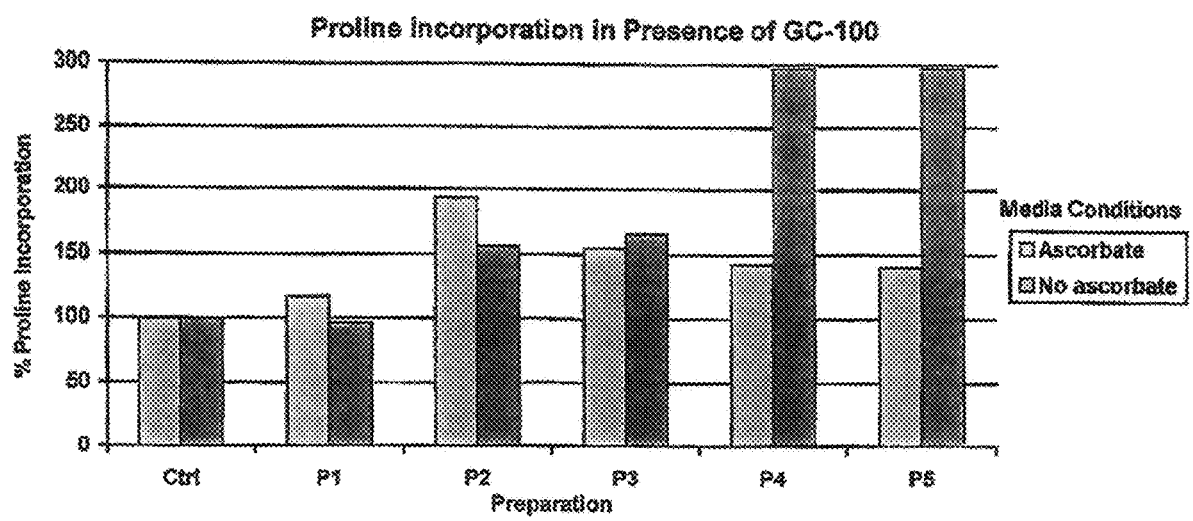
FIG. 7 is a graph showing proline incorporation in the presence of GC-100, according to an embodiment.
Figure 8:
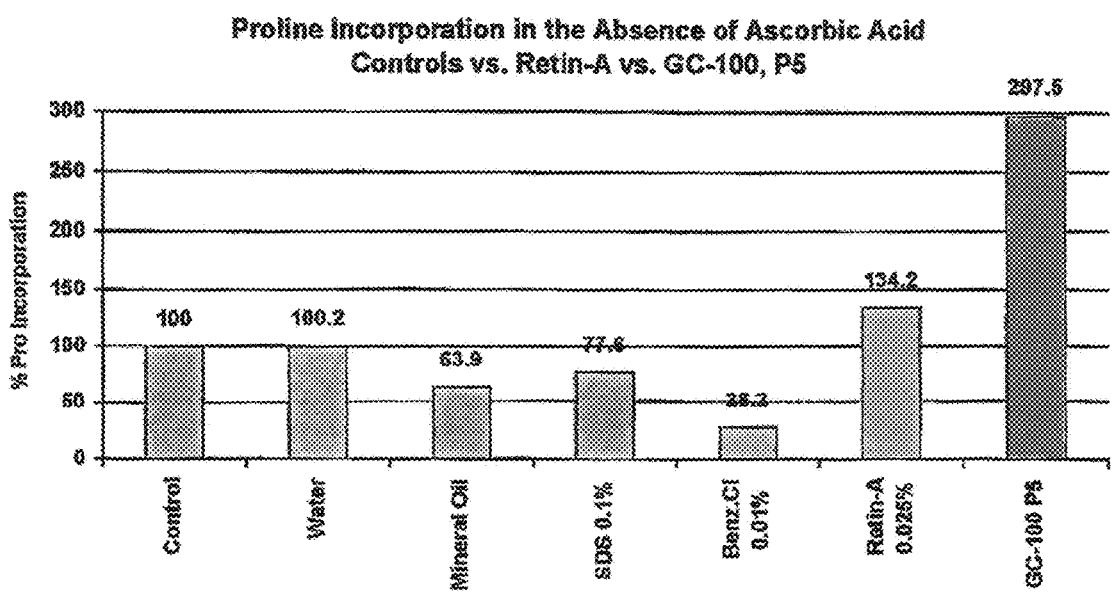
FIG. 8 is a graph showing proline incorporation in the absence of asborbic acid for controls, Retin-A and GC-100, according to an embodiment.

FIGS. 7 and 8 show that the amount of proline incorporation in the absence of ascorbic acid is higher than in the presence of ascorbic acid. GC-100 provides better supplementation for proline incorporation in the absence of additional ascorbic acid, which is a precursor for collagen synthesis. Ascorbic acid clearly influences proline incorporation: higher than optimal concentrations of ascorbic acid suppress proline incorporation. GC-100 preparations generate more than twice the proline incorporation of Retin-A 0.025% in vitro. Mineral oil, rubbing alcohol, and benzyl chloride suppress proline incorporation below control levels.

The anti-inflammatory activity of GC-100 was evaluated using ultraviolet-induced erythema as an endpoint.

Ultraviolet radiation generates a predictable, dose-dependent cutaneous response over time. The pathological mechanism includes injury to epidermal, dermal, and vascular constituents of the skin with a local inflammatory response mediated by proinflammatory cytokines and prostaglandins. It is the objective of this experiment to determine whether GC-100 can alleviate an ultraviolet-mediated inflammatory response by qualitative assessment

| SKIN SQUARE | TEST AGENT |
|---|---|
| 1 | Control |
| 2 | Placebo |
| 3 | 0.1% GC-100 |
| 4 | 0.5% GC-100 |
| 5 | 1.0% GC-100 |
| 6 | Untreated |

Erythema was quantified after 2, 4, 5, and 24 hours following irradiation using a standard erythema scale that has been shown historically to yield reproducible results.

| ERYTHEMA SCORE | ERYTHEMA EQUIVALENT |
|---|---|
| 0 | None |
| 1 | Questionable |
| 2 | Mild |
| 3 | Moderate |
| 4 | Severe |

| | ERYTHEMA SCORE (MEAN ± SD) | | | |
|---|---|---|---|---|
| [GC-100] | 2 HRS | 4 HRS | 5 HRS | 24 HRS |
| Control | 2.78 ± 0.44 | 3.78 ± 0.94 | 4 | 2 |
| Placebo | 2.78 ± 0.44 | 3.67 ± 0.50 | 4 | 2.11 |
| 0.1% | 1.89 ± 0.60 | 1.56 ± 0.53 | 1.67 ± 0.71 | 1.00 ± 0.71 |
| | 32% | 58.7% | 58.3% | 50% |
| 0.5% | 1.22 ± 0.44 | 1.56 ± 0.53 | 1.56 ± 0.53 | 0.89 ± 0.33 |
| | 56.1% | 58.7% | 58.7% | 55.5% |
| 1.0% | 1.00 | 1.22 ± 0.44 | 1.33 ± 0.50 | 0.33 ± 0.50 |
| | 64% | 67% | 66.81% | 83.5% |

Figure 9:
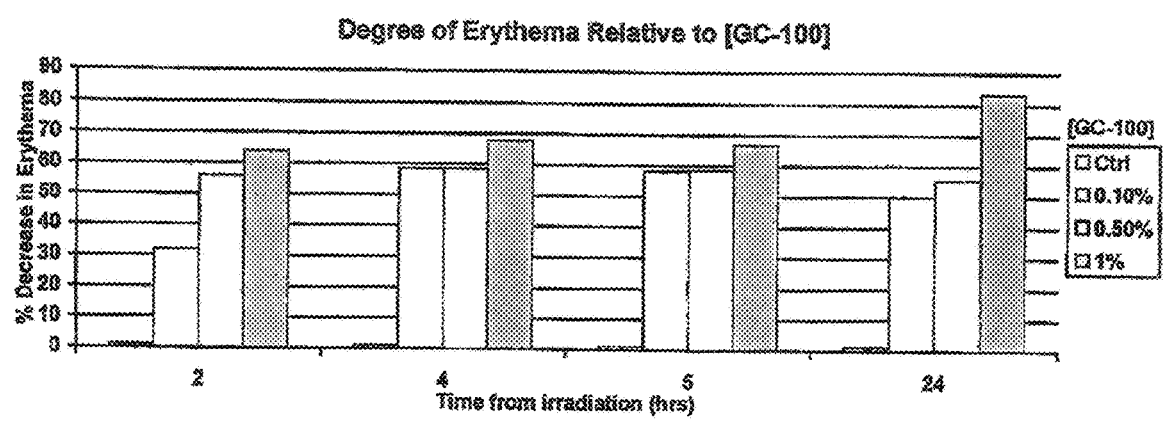
FIG. 9 is a graph showing the degree of erythema relative to GC-100 concentration, according to an embodiment.

FIG. 9 is a graph showing the degree of erythema relative to GC-100 concentration. GC-100 exhibits an ability to suppress ultraviolet-induced erythema. The results of this experiment suggest that the potency of any anti-inflammatory effect is dose dependent, with greatest activity noted with 1% GC-100, followed sequentially by 0.5% and then 0.1%. The different concentration of GC-100 was not found to be statistically significant.

To establish the anti-inflammatory potential of GC-100 by measuring the inhibition of $PGE_2$ synthesis by 3T3 fibrosis in cell culture. This test attempts to demonstrate a decrease in the production of eicosanoids by 3T3 fibroblasts in culture that are exposed to GC-100. The cells are nourished in a medium enriched with arachidonic acid which leads to increased secretion of eicosanoids into the medium.

The formation of prostaglandin $PGE^2$ will be followed as a marker of eicosanoid synthesis, because it is a stable molecule secreted preferentially by 3T3 fibroblasts. The anti-inflammatory potential of an active ingredient may then be investigated by following the decrease in secretion of $PGE^2$ in the culture medium.

Quantification of $PGE^2$ will be achieved using an enzyme-linked immunosorbant assay (ELISA). In principle, the $PGE_2$ expressed by the cells in culture medium will compete with enzyme-linked $PGE_2$ for available antibody, which is a constant. The concentration of enzyme linked to $PGE_2$ prior to testing is acetylcholinesterase. Since the quantity of $PGE_2$ expressed by 3T3 cells in culture will vary based on the concentration of GC-100 present, the amount of antibody available to bind to the enzyme-linked PGE2 versus that produced by the 3T3 cells assumes an inverse relationship that is dependent on Brownian motion. After eliminating unreacted $PGE_2$ through washing, substrate is added that binds to the enzyme-$PGE_2$-antibody complex to generate a yellow color that is strongly evident using spectrophotometer set at 412 nm. The amount of light transmitted through the test sample is directly proportional to the intensity of the color change and, consequently, to the concentration of $PGE_2$-enzyme-antibody complex.

Example 5: Inhibition of Cyclooxygenase

This Example establishes the anti-inflammatory potential of GC-100 by measuring the inhibition of $PGE_2$ synthesis by 3T3 fibroblasts in cell culture.

This test attempts to demonstrate a decrease in the production of eicosanoids by 3T3 fibroblasts in culture that are exposed to GC-100. The cells are nourished in a medium enriched with arachidonic acid which leads to increased secretion of eicosanoids into the medium.

The formation of prostaglandin $PGE_2$ will be followed as a marker of eicosanoid synthesis, because it is a stable molecule secreted preferentially by 3T3 fibroblasts. The anti-inflammatory potential of an active ingredient may then be investigated by following the decrease in secretion of $PGE_2$ in the culture medium.

Quantification of $PGE_2$ will be achieved using an enzyme-linked immunosorbant assay (ELISA). In principle, the $PGE_2$ expressed by the cells in culture medium will compete with enzyme-linked $PGE_2$ for available antibody, which is a constant. The concentration of enzyme-linked $PGE_2$ is also constant and quantified prior to testing. The enzyme linked to $PGE_2$ prior to testing is acetylcholinesterase. Since the quantity of $PGE_2$ expressed by 3T3 cells in culture will vary based on the concentration of GC-100 present, the amount of antibody available to bind to the enzyme-linked $PGE_2$ versus that produced by the 3T3 cells assumes an inverse relationship that is dependent on Brownian motion. After eliminating unreacted $PGE_2$ through washing, substrate is added that binds to the enzyme-$PGE_2$-antibody complex to generate a yellow color that is strongly evident using spectrophotometer set at 412 nm. The amount of light transmitted through the test sample is directly proportional to the intensity of the color change and, consequently, to the concentration of $PGE_2$-enzyme-antibody complex.

Materials & Methods

Create a mother solution (solution #1) containing complete DMEM, alcohol, and $2 \times 10^5$ 3T3 fibroblasts for plating onto 25 $cm^2$ culture dishes. Using a compounding dilution technique, prepare the following solutions, using 5 mL of media per plate:

Solution #2: Solution #1 plus arachidonic acid ($10^{-3}$% P/V)

Solution #3: Solution #2 plus indomethacin (0,1,$10^{-3}$% P/V)

Solution #4: Solution #2 plus GC-100 0.5%

Solution #5: Solution #2 plus GC-100 1.0%

Figure 10:
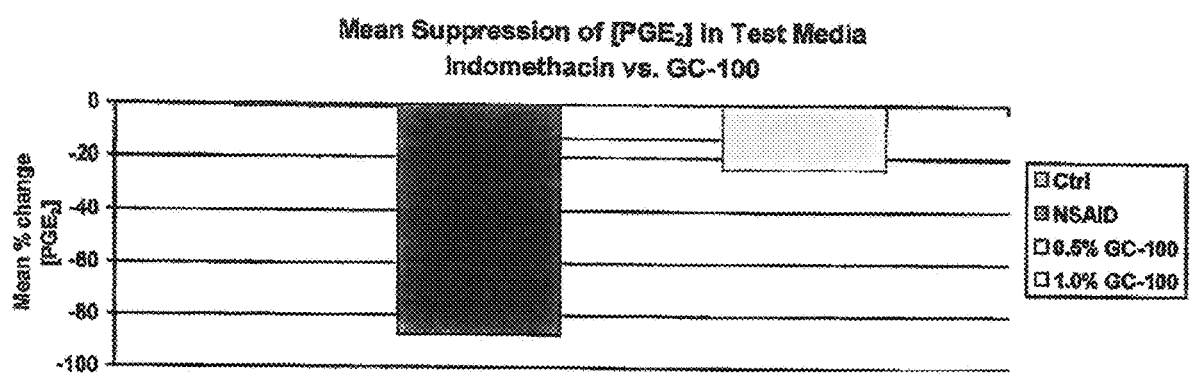
FIG. 10 is a graph showing mean suppression of $PGE_2$ concentration in test media comprising indomethacin or GC-100, according to an embodiment.

Incubate all preparations for 24 hours at 37° C. Recover the supernatant media, and if needed deep freeze it at −20° C. before quantification. Count the number of surviving cells using a coulter counter. Establish a calibration curve of the quantity of $PGE_2$. Quantify the supernatant media using an enzyme-linked immunosorbant assay kit specific for $PGE_2$ (Cayman), using a Dynotech microplate reader (MR500) with a filter set at 412 nm. Calculate the % inhibition of $PGE_2$ synthesis. The results are shown in Table 4 and FIG. 10, which is a graph showing mean suppression of $PGE_2$ concentration in test media comprising indomethacin or GC-100.

TABLE 4

| | [$PGE_2$ pg/mL] and % change* | | | |
|---|---|---|---|---|
| TEST CONDITIONS | A | B | C | MEAN |
| DMEM + Alcohol | 0.55 | 0.41 | 0.37 | |
| DMEM + AA | 3.14 | 3.00 | 2.87 | 0 |
| | 0% | 0% | 0% | |
| DMEM + AA + Indomethacin | 0.27 | 0.35 | 0.50 | −87.2 |
| | −91% | −88% | −82.6% | |
| DMEM + AA + 0.5% GC-100 | 2.81 | 2.41 | 2.62 | −13 |
| | −10.5% | −19.7% | −8.7% | |
| DMEM + AA + 1% GC-100 | 2.39 | 2.17 | 2.29 | −23.9 |
| | −23.9% | −27.7% | −20.2% | |

*Percent of variation = (DMEM + AA + agent)/(DMEM + AA) × 100

GC-100 suppresses the expression of PGE$_2$ by 3T3 fibroblasts in cell culture. GC-100 1% decreases expression of PGE$_2$ a mean of 24% below untreated control, in comparison to 87% suppression by indomethacin.

Example 6: Tyrosinase Activity

This Example establishes and quantifies the effect of GC-100 on tyrosinase synthesis in B$_{16}$ melanoma cells.

It has been reported that tyrosinase in synthesized in B$_{16}$ melanoma cells within 24 hours of plating. On the basis of these reports, B$_{16}$ melanoma cells were used to evaluate the inhibitory effects of GC-100 on tyrosinase synthesis. As an indication of tyrosinase synthesis, tyrosinase activity in B$_{16}$ melanoma cells was measured in addition to the amount of melanin synthesized per cell.

Materials & Methods

B$_{16}$ melanoma cells ($5.0' \times 10^4$) were incubated in a 96-well microplate supplemented with DMEM and 5% fetal calf serum at 37° C. for 24 hours. Incubation was continued for an additional 24 hours at 37° C. in DMEM supplemented with GC-100 at either 250 µg/mL, 500 µg/mL, or 1000 µg/mL. After washing cells with PBS twice, the cells were lysed with 50 µL of phosphate buffer (0.05 mM, pH 6.8) containing 0.1% Triton-X, and incubated at 37° C. for 30 minutes. Then 100 µL of phosphate buffer (0.1 mM, pH 6.8) containing 0.1% DOPA was added to the lysate and incubated at 37° C. for 3 hours. The resultant melanin content and protein content of the lysate were then quantified.

Figure 11:
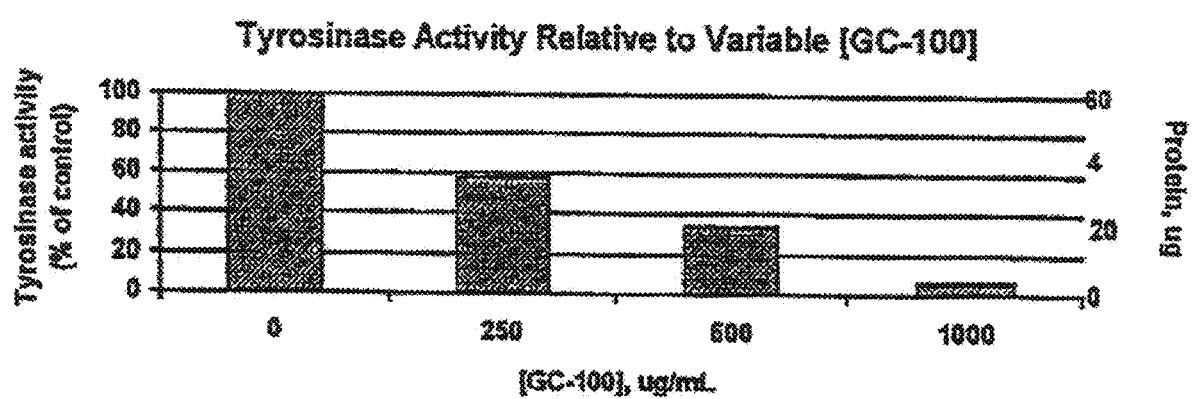
FIG. 11 is a graph showing tyrosinase activity as a function of GC-100 concentration, according to an embodiment.

GC-100 selected for examination was quantitatively evaluated regarding its inhibitory activity of melanogenesis in B$_{16}$ melanoma cells. B$_{16}$ melanoma cells were seeded into a 60 mm diameter dish at density of $1.5' \times 10^5$ cells/dish and incubated at 37° C. in DMEM supplemented with 10% FCS and 40 mM sodium lactate. After 4 days, the medium was exchanged to DMEM supplemented with 5% FCS and the aforementioned concentrations of GC-100 and cultured at 37° C. The results are shown in Table 5 and FIG. 11, which is a graph showing tyrosinase activity as a function of GC-100 concentration.

TABLE 5

| [GC-100], µg/mL | TYROSINASE ACTIVITY (% of untreated control) |
|---|---|
| 0 | 100 |
| 250 | 57.3 ± 12% |
| 500 | 34.1 ± 14% |
| 1000 | 6.6 ± 14.8% |

Example 7: Clinic Trial on Photoaged Skin

A pilot open label study was conducted to establish the efficacy of GC-100 on photoaged skin in a clinical setting.

There are a number of products such as alpha-hydroxy acid and retinoic acid derivatives that have been shown to reverse the signs and symptoms of dermatoheliosis, thereby improving the cosmetic appearance of the skin. The efficacy of topical GC-100 in treating dermatoheliosis is well established in in vitro studies. This protocol was conducted in order to verify the activity of GC-100 on photodamaged human skin.

GC-100 is supposed to improve the cosmetic appearance of the skin—namely, to decrease the appearance of wrinkles. It would appear that the decrease in wrinkles anticipated by using GC-100 should be secondary to novel collagen synthesis according to in vitro studies. However, it is unclear whether the apparent decrease in skin wrinkles would be due to new collagen deposition or to a mild clinical irritation with edema as commonly seen with other anti-aging preparations. The purpose of this study is therefore also to determine whether the decreased appearance of skin wrinkles observed after treatment with GC-100 is due to new collagen deposition or clinical irritation.

Primary endpoints for this study were as follows:
1. Epidermal skin thickness was measured using high frequency ultrasound.
2. Panelists regard for their overall appearance and any changes noted in the appearance of their wrinkles, lentigines, facial acne and pore size were used in qualitative analysis. In addition, panelists were asked to comment on irritation, novel rashes, and other side effects during the study period.

Materials & Methods

An open label, six week pilot study to examiner the regenerative effect of GC-100 was performed on 15 women with mild to moderate dermatoheliosis as defined by clinical examination. Exclusion criteria selected against patients with a history of retinoic acid use, dermabrasion, or chemical peel application within 6 months prior to study onset. However, all patients had used one or more of these products previously. After appropriate informed consent was obtained, baseline measurements of epidermal thickness using high frequency untrasonography (20 MHz and above) were collected using skin at the infraorbital prominence. Three measurements were taken at each site and averaged to yield a result. GC-100 was applied to the face and neck according to the following schedule:

Weekly: GC-100 applied in mask vehicle
Twice daily: GC-100 applied through lotion vehicle The patient population was divided into two groups, where Group I was evaluated after 24 hours of product application, and Group II was evaluated at the conclusion of weeks 2, 4 and 6. A panelist questionnaire was completed during each evaluation session. The results are shown in Tables 6 and 7.

TABLE 6

|  | Group I | Group II |
|---|---|---|
| Panelists | 9 | 6 |
| Age | 30-60 | 35-40 |
| % change | 3.4-19.2 | 2.9-14 |
| Mean % | 8.5 | 7.95 |

TABLE 7

| ENDPOINT QUESTIONS | POSITIVE RESPONSE |
|---|---|
| Improved overall cosmetic appearance | 92% |
| Decreased appearance of wrinkles | 62% |
| Decreased appearance of lentigines | 54% |
| Decreased incidence of blemishes | 92% |
| Decreased appearance of pores | 92% |
| Incidence of side effects | 0% |

Statistical Significance of Qualitative Results: P=0.0225 by Wilcoxan rank sum test.

GC-100 is responsible for clinical improvement of dermatoheliosis and intrinsic aging without causing irritation. No clinically detectable irritation occurred at any time during the study.

In both treatment groups, there was a significant increase over baseline of stratum corneum compaction spongiosis, granular cell layer thickness and epidermal thickness due to collagen production as seen with high frequency ultrasound. The GC-100 therefore appears to have potent skin rejuvenating biological activity.

Light Microscopy

Skin tissue treated with GC-100 in the absence of ascorbic acid was prepared to illustrate collagen deposition. Tissue samples were first pretreated with Bouin's solution to intensify subsequent staining results. Samples were then treated with Mason's trichrome stain, which combines the plasma stain (chromotrope 2R) and connective tissue fiber stain) aniline blue) in a phosphotungstic acid solution to which glacial acetic acid was added. The collagen absorbs the tungsten ion, which may be visualized due to the complexed aniline blue.

Staining for specific collagen types was achieved using specific standardized indirect immunoperoxidase attains for collagen I and III, respectively.

Collagen deposition assessments are based on the visual interpretation of two endpoints: Collagen I and Collagen III. An untreated control and a tissue sample treated with GC-100 were stained to reveal collagen I. A similar method of comparison was used to illustrate collagen III deposition in control and treated tissue.

Electron Microscopy

Tissues used for light microscopy were place in Karnovsky's fixative for additional evaluation using electron microscopy standard technique. Magnification power of 20,000× was used for visualization of the lower dermis.

Photographs of the lower dermis at 20,000× illustrate the change in collagen deposition characteristics in the presence of GC-100. The dark fragments and lines represent collagen fibers. In the untreated control, the density of collagen fibers is low, and broken collagen fragments predominate. In the tissue treated with GC-100, collagen fiber density is increased, collagen fibers become elongated and the collagen triple helical structure becomes readily apparent.

Example 8: Compositions

This Example provides exemplary compositions for improving skin hydration.

TABLE 8

| Ingredient | Concentration (wt %) |
| --- | --- |
| Deionized Water | qs |
| Yam extract | 15 |
| Safflower oil | 3 |
| Glycerin | 3 |
| Glyceryl stearate | 2.5 |
| Cetyl alcohol | 2 |
| Shea butter | 2 |
| Avocado oil | 2 |
| Stearic acid | 2 |
| Kukui nut oil | 2 |
| TEA-Hydroiodide | 1 |
| Ruscus extract | 1 |
| Ivy extract | 1 |
| Indies chestnut extract | 1 |
| Gingko extract | 1 |
| Fucus vesiculosus extract | 1 |
| Essential oils | 0.5 |
| Polypeptide (Aspartic acid, Histidine, D-Phenylalanine, Arginine, Tryptophan) | 0.5 |
| Lys-Pro, Gly complex | 0.5 |
| Imidazolidinyl urea | 0.5 (optional) |
| Methylparaben | 0.5 (optional) |

TABLE 8-continued

| Ingredient | Concentration (wt %) |
| --- | --- |
| Propylparaben | 0.5 (optional) |
| Potassium sorbate | 0.5 (optional) |
| Butylated hydroxytoluene (BHT) | 0.5 (optional) |
| Phenoxyethanol | 0.5 (optional) |
| Caprylyl glycol | 0.5 (optional) |
| Hexylene glycol | 0.5 (optional) |
| Ethylhexylglycerin | 0.5 (optional) |

The exemplary composition may be made by combining the ingredients in Table 8 in a single vessel. The ingredients may be added in any order and mixed by magnetic or mechanical stirring (e.g., paddle, whisk, rotary screw) at medium to high speed for between 5 minutes and 1 hour until evenly distributed.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, and method steps set forth in the present description. As will be apparent to one of skill in the art, methods and devices useful for the present methods and devices can include a large number of optional composition and processing elements and steps.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a peptide" includes a plurality of such peptides and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is/are not specifically disclosed herein.

All art-known functional equivalents of materials and methods are intended to be included in this disclosure. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

What is claimed is:

1. A topical formulation comprising:
    a dipeptide having a sequence of Lys-Pro;
    a polypeptide having a sequence of Asp-His-D-Phe-Arg-Trp (SEQ ID NO: 1); and
    at least one bioflavonoid in a cosmetically or pharmaceutically acceptable carrier.

2. The topical formulation of claim 1, wherein the at least one bioflavonoid is a bioflavonoid extract.

3. The topical formulation of claim 1, wherein the at least one bioflavonoid is selected from the group consisting of flavones, flavonols, flavanones, flavanols, anthocyanins and isoflavones.

4. The topical formulation of claim 1, wherein the at least one bioflavonoid is derived from a source selected from the group consisting of yam, ruscus, ivy, Indies chestnut, fucus vesiculosus, broccoli, parsley, thyme, legumes, buckwheat, berries, bananas, citrus fruits, onion, red wine, dark chocolate, tea, or Ginko *biloba*.

5. The topical formulation of claim 1, wherein the at least one bioflavonoid is a yam extract.

6. The topical formulation of claim 1, wherein the at least one bioflavonoid is present in a concentration between 2 wt % and 30 wt %.

7. The topical formulation of claim 1, wherein the dipeptide and the at least one bioflavonoid are present in a weight ratio between 1:30 and 1:3.

8. The topical formulation of claim 1, wherein the dipeptide and the at least one bioflavonoid are present in a weight ratio of 1:9.

9. The topical formulation of claim 1, wherein the dipeptide and the at least one bioflavonoid are present in the topical formulation at a concentration between 10% by weight and 25% by weight.

10. The topical formulation of claim 1, further comprising at least two bioflavonoids.

11. The topical formulation of claim 1, further comprising one or more of ruscus extract, ivy extract, Indies chestnut extract, gingko extract, and fucus vesiculosus extract.

12. The topical formulation of claim 1, further comprising an amino acid selected from the group consisting of glycine, alanine, proline and combinations thereof.

13. The topical formulation of claim 12, wherein the amino acid is complexed with the dipeptide.

14. The topical formulation of claim 1, wherein the amino acid and the dipeptide are covalently bound to one another, or wherein the amino acid and the dipeptide are ionically bound to one another, or wherein the amino acid and the dipeptide are electrostatically attracted to one another.

15. The topical formulation of claim 1, wherein the cosmetically or pharmaceutically acceptable carrier is selected from the group consisting of water, an organosilicone compound, a silicone elastomer, a $C_6$-$C_{28}$ linear hydrocarbon and combinations thereof.

16. A method of hydrating skin in a subject in need thereof, said method comprising administering to the subject a therapeutically effective amount of the topical formulation of claim 1.

17. The method of claim 16, wherein the therapeutically effective amount is administered in portions once daily, twice daily or three times daily.

18. The method of claim 16, wherein the topical formulation is administered topically or transdermally.

19. The method of claim 18, wherein the topical formulation is administered as a lotion, an oil, a cream, a butter, or a serum.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: SITE
<222> LOCATION: (3)..(3)
<223> OTHER INFORMATION: D-Phenylalanine

<400> SEQUENCE: 1

Asp His Phe Arg Trp
1               5
```